United States Patent [19]

Archibald et al.

[11] 4,105,771
[45] Aug. 8, 1978

[54] 1-AMINOALKYLPIPERIDINE DERIVATIVES

[75] Inventors: John Leheup Archibald, Windsor; Terence James Ward, Cippenham, both of England

[73] Assignee: John Wyeth & Brother Limited, Maidenhead, England

[21] Appl. No.: 805,203

[22] Filed: Jun. 9, 1977

[30] Foreign Application Priority Data

Jun. 23, 1976 [GB] United Kingdom ............... 26099/76

[51] Int. Cl.$^2$ ........................................... C07D 211/58
[52] U.S. Cl. ............................... 424/267; 260/293.77; 260/293.67; 260/293.68; 260/293.69; 260/293.71
[58] Field of Search .................... 260/293.77; 424/267

[56] References Cited

U.S. PATENT DOCUMENTS 3,992,389  11/1976  Cavalla et al. .................. 260/293.77

Primary Examiner—Norma S. Milestone
Attorney, Agent, or Firm—Arthur E. Wilfond

[57] ABSTRACT

This invention relates to compounds having the formula

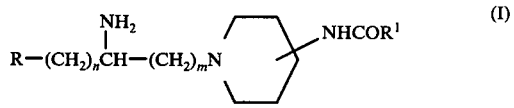

and the pharmaceutically acceptable acid addition and quaternary ammonium salts thereof, wherein R represents phenyl or phenyl substituted by halogen, lower alkyl, hydroxy, trifluoromethyl or lower alkoxy; $n$ represents 0 or 1 and $m$ represents 2 or 3 with the proviso that $n$ plus $m$ equals 3; and $R^1$ represents phenyl, thienyl, pyridyl, furyl, indolyl or phenyl substituted by halogen, lower alkyl, lower alkoxy, trifluoromethyl or hydroxy, which exhibit antihypertensive activity in warm blooded animals.

6 Claims, No Drawings

1-AMINOALKYLPIPERIDINE DERIVATIVES

This invention relates to piperidine derivatives which possess pharmacological activity, to processes for preparing them and to pharmaceutical compositions containing them.

U.K. patent specification No. 1,345,872 discloses (inter alia) 2,3 or 4 acylamino-1-(aryl lower alkyl)piperidine derivatives which possess anti-inflammatory and/or action on the cardiovascular system.

This invention provides piperidine derivatives having the formula

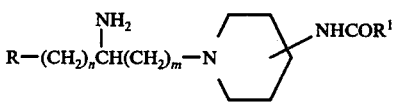
(I)

wherein R represents phenyl or phenyl substituted by halogen, lower alkyl, hydroxy, trifluoromethyl or lower alkoxy, $R^1$ represents phenyl, thienyl, furyl, pyridyl, indolyl or phenyl substituted by halogen, lower alkyl, lower alkoxy, trifluoromethyl or hydroxy, $n$ represents 0 or 1 and $m$ represents 2 or 3; with the proviso that $n$ plus $m$ equals 3, and the pharmaceutically acceptable acid addition and quaternary ammonium salts thereof.

The phenyl radical R may be substituted by one or more groups such as halogen, (e.g. fluorine or chlorine) lower alkoxy (e.g. methoxy, ethoxy, propoxy, butoxy) hydroxy, lower alkyl, e.g. methyl, ethyl, propyl or butyl, and trifluoromethyl.

The term "lower" used in relation to alkyl and alkoxy radicals means that such radicals contain from 1 to 6, preferably 1 to 4 carbon atoms.

Examples of radicals for $R^1$ are phenyl, 2-thienyl, 2-pyridyl, 2-furyl and phenyl substituted by one or more groups as mentioned above for the radical R.

Preferred values for $n$ and $m$ are 0 and 3 respectively.

Preferably the —$NHCOR^1$ substituent is in the 4-position on the piperidine ring. Preferably R is phenyl, hydroxyphenyl, halophenyl, lower alkyl phenyl, or lower alkoxy phenyl and preferably $R^1$ is phenyl, halophenyl, lower alkoxy phenyl or lower alkyl phenyl.

Examples of the pharmaceutically acceptable acid addition salts are those formed from inorganic and organic acids, in particular an acid selected from sulphuric, hydrochloric, hydrobromic, hydroiodic, nitric, phosphoric, sulphonic (such as methane sulphonic and p-toluene sulphonic,) acetic, maleic, fumaric, tartaric and formic acids.

The compounds of formula I possess pharmacological activity, in particular action on the cardiovascular system, especially antihypertensive activity, when tested on warm blooded animals. Compounds of formula I were tested for antihypertensive activity by administering them orally to spontaneously hypertensive rats.

Representative of the antihypertensive compounds of this invention is 4-benzamido-1-(4-amino-4-phenylbutyl)piperidine which produced a marked decrease in blood pressure of 24% when administered at a dose level of 50 mpk in the above test.

It will be apparent to those skilled in the art that the compounds of formula I possess an asymmetric centre and therefore optical isomers are possible. It is to be understood that such isomers and mixtures thereof, e.g. racemates, are included within the scope of this invention, Methods for resolving mixtures of optical isomers are well known in the art. Such optical isomers of formula I compounds are prepared by resolution techniques to obtain the individual enantiomers.

One process for preparing compound of formula I comprises reducing a compound of formula

(II)

wherein R, $R^1$, $n$ and $m$ are as defined above. The reduction may be carried out by treating the oximes with hydrogen in the presence of a Raney nickel catalyst.

The reduction may also be carried out with an alkali metal, preferably sodium in an alkanol, for example ethanol or isopropanol.

In a preferred embodiment the reduction of oximes of formula II is carried out by generating a Raney nickel catalyst and hydrogen in situ. This may be effected by adding nickel/aluminium alloy to a solution of the oxime in a reaction inert solvent, such as an alkanol, e.g. ethanol, in the presence of sodium hydroxide.

The compounds of formula II may be prepared by routes disclosed in U.K. patent specification No. 1,345,872 and also in our copending U.S. Pat. application Ser. No. 805,202 filed on the same day as the present application under the title "1-Hydroxyiminoalkyl-4-benzamidopiperidine derivatives" by J. L. Archibald and T. J. Ward.

One such process comprises reacting the corresponding ketone with hydroxylamine in the presence of NaOH.

A further process for preparing compounds of formula I wherein $n$ is 1 and $m$ is 2 comprises reacting a ketone of formula

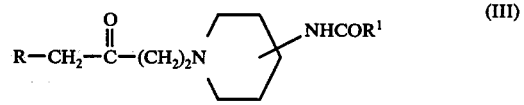
(III)

wherein R and $R^1$ are as defined above, with an alkali metal cyanoborohydride, for example, sodium cyanoborohydride plus an ammonium salt. Such a reaction may be carried out at pH about 4 to 10, preferably 6 to 8, in lower alkanol solvent, e.g. methanol. The ammonium salt is preferably ammonium acetate.

The compounds provided by the invention form acid addition salts with acids (particularly pharmaceutically acceptable acids) or quaternary ammonium salts, for example with alkyl halides or aralkyl halides (particularly methyl iodide or benzyl chloride or bromide). A free base may be treated with the appropriate acid in the presence of a suitable solvent to give an acid addition salt. The quaternary salts may be prepared by treating the free base with the appropriate halide in the presence or absence of a solvent.

The invention also includes pharmaceutical compositions containing as active ingredient an active compound of formula I as defined above. The compound may be micronised if desired. In addition to the active ingredient, the compositions also contain a non-toxic carrier. Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or table-disintegrating agents; it can also be an encapsulating materials. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax and cocoa butter. The term "composition" is intended to include the formation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. When the active ingredient is sufficiently soluble it can be dissolved in normal saline as a carrier; if it is too insoluble for this it can often be dissolved in a suitable organic solvent, for instance aqueous propylene glycol or polyethylene glycol solutions. Aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilised by intramuscular, intraperitoneal or subcutaneous injection. In many instances, a compound is orally active and can be administered orally either in liquid or solid composition form.

Preferably the pharmaceutical composition is in unit dosage form. In such form the composition is subdivided in unit doses containing appropriate quantities of the active ingredients; the unit dosage form can be a packaged composition, the package containing specific quantities of composition, for example packeted powders or vials or ampoules. The unit dosage form can be a capsule, cachet or tablet itself, or it can be the appropriate number of any of these in package form. The quantity of active ingredients in a unit dose of composition may be varied or adjusted from 5 mg. or less to 500 or more, according to the particular need and the activity of the active ingredient. The invention also includes the compounds in the absence of carrier where the compounds are in unit dosage form.

The following examples illustrate the invention:

EXAMPLE 1

4-Benzamido-1-(4-amino-4-phenylbutyl)piperidine

Nickel/aluminium alloy (2.5 g) was added portionwise over 10 minutes to a suspension of 4-benzamido-1-(4-hydroxyimino-4-phenylbutyl)piperidine (0.5 g, 1.37 mmol) in a mixture of I.M.S.*(40 cm$^3$), water (10 cm$^3$), and aqueous sodium hydroxide (50 cm$^3$, 10% w/v).

* IMS = Industrial methylated spirit.

After addition was complete aqueous sodium hydroxide (30 cm$^3$, 10% w/v) was added and the reaction stirred for 30 minutes. The catalyst was then removed by filtration, the filtrate was evaporated and the residue partitioned between ether and water. The ether extract was dried and evaporated to yield the title compound (0.277 g, 58%) as the free base. This was dissolved in ethanolic hydrogen chloride and the ethanol was evaporated while the volume of solution was maintained by addition of ethyl acetate. On standing overnight the crystalline dihydrochloride of the title compound separated.

Melting point 264.0° C.

Analysis: Found: C, 61.70; H, 7.30, N, 9.70. $C_{22}H_{29}N_3O.2HCl.\frac{1}{4}H_2O$ requires: C, 61.61; H, 7.40; N, 9.80%.

EXAMPLE 2

Using a process analogous to Example 1 the following compounds of formula I may be prepared according to the reaction:

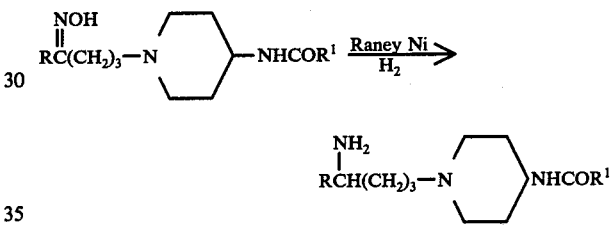

wherein:

| R | R$^1$ |
|---|---|
| phenyl | 2-thienyl |
| phenyl | p-chlorophenyl |
| p-fluorophenyl | phenyl |
| phenyl | p-methoxyphenyl |
| p-hydroxyphenyl | phenyl |
| m-tolyl | phenyl |
| p-methoxyphenyl | p-tolyl |

The oxime starting materials used above may be prepared by the general process of reacting the corresponding ketone with hydroxylamine in the presence of sodium hydroxide.

We claim:

1. A compound having the formula

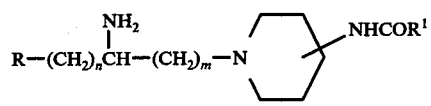

and the pharmaceutically acceptable acid addition and quaternary ammonium salts thereof, wherein NHCOR$^1$ is in the 4-position; R represents phenyl or phenyl substituted by halogen, lower alkyl, hydroxy, trifluoromethyl or lower alkoxy; n represents 0 or 1 and m represents 2 or 3 with the proviso that n plus m equals 3; and R$^1$ represents phenyl or phenyl substituted by halogen, lower alkyl, lower alkoxy, trifluoromethyl or hydroxy.

2. A compound according to claim 1 wherein R is phenyl, hydroxyphenyl, loweralkylphenyl or lower alkoxy phenyl.

3. A compound according to claim 1 wherein $R^1$ is phenyl, halophenyl, loweralkoxyphenyl or lower alkylphenyl.

4. A compound according to claim 1 wherein $n$ is 0 and $m$ is 3.

5. A compound according to claim 1 which is 4-benzamido-1-(4-amino-4-phenylbutyl)piperidine.

6. An antihypertensive pharmaceutical composition comprising a therapeutically effective amount of a compound as claimed in claim 1 or a pharmaceutically acceptable acid addition or quaternary ammonium salt thereof together with a pharmaceutically acceptable carrier.

* * * * *